US011723419B2

(12) United States Patent
Joy

(10) Patent No.: US 11,723,419 B2
(45) Date of Patent: Aug. 15, 2023

(54) FINGER SLEEVE FOR EAR CLEANING

(71) Applicant: Suzanne Joy, Wexford, PA (US)

(72) Inventor: Suzanne Joy, Wexford, PA (US)

(*) Notice: Subject to any disclaimer, the term of this patent is extended or adjusted under 35 U.S.C. 154(b) by 699 days.

(21) Appl. No.: 16/357,530

(22) Filed: Mar. 19, 2019

(65) Prior Publication Data
US 2019/0281906 A1 Sep. 19, 2019

Related U.S. Application Data

(60) Provisional application No. 62/645,107, filed on Mar. 19, 2018.

(51) Int. Cl.
A41D 13/08 (2006.01)
A61F 11/00 (2022.01)

(52) U.S. Cl.
CPC .......... *A41D 13/087* (2013.01); *A61F 11/006* (2013.01)

(58) Field of Classification Search
CPC ....... A41D 13/087; A47K 7/02; A61F 11/006; A61F 13/38; A61F 13/22
USPC .......................................... 640/1, 2; 606/162
See application file for complete search history.

(56) References Cited

U.S. PATENT DOCUMENTS

| 6,647,549 | B2* | 11/2003 | McDevitt | A41D 13/087 2/21 |
| 7,696,111 | B2* | 4/2010 | Mangold | D04H 1/492 442/344 |
| 7,789,845 | B1* | 9/2010 | Meliti | A61F 13/38 2/163 |
| 2017/0304120 | A1* | 10/2017 | Seifert | B65D 85/62 |

* cited by examiner

*Primary Examiner* — Benjamin J Klein
*Assistant Examiner* — Hans Kaliher
(74) *Attorney, Agent, or Firm* — Blynn L. Shideler; Krisanne Shideler; BLK Law Group

(57) ABSTRACT

A finger sleeve for cleaning or drying the outer human ear.

4 Claims, 6 Drawing Sheets

FINGER SLEEVE FOR EAR CLEANING

CROSS-REFERENCE TO RELATED APPLICATIONS

This application claims the benefit of PPA Ser. No. 62/645,107 filed on Mar. 19, 2018.

FIELD OF INVENTION

The present invention relates to ear cleaning devices and to a device that accommodates at least one finger that is adapted to clean or dry the outer human ear. More generally, the device of the invention can be used for cleaning mammalian ears, including but not limited to humans, dogs, and cats. It can be safely and effectively used on babies, toddlers, children, and adults.

BACKGROUND

Varieties of cloths, wipes, swabs, and other ear cleaners have been developed to clean ears. Known ear cleaners generally consist of either a fabric cloth to wipe the folds of the outer ear or a rigid device that extends into the ear canal and may compact ear wax or puncture the eardrum.

This invention provides an ear-cleaning device comprised of soft fabric that can extend into the ear canal and remove ear wax without rigid components.

SUMMARY

The present invention provides for an ear-cleaning device adapted to a user's finger that allows the safe cleaning of an outer ear without discomforting or injuring the ear. The invention comprises a tubular finger sleeve made of textured fabric and includes a soft insert in the tip of the sleeve that allows a user to clean an ear.

DETAILED DESCRIPTION OF THE INVENTION

The ear is a sensitive, delicate, and complex organ that is difficult for young children to clean without discomfort or injury. Currently, to clean ears, most adults and children use washcloths. Generally, parents of young children will clean their children's ears because children are reluctant or unable to clean their own.

The most common ear-cleaning device is a simple wetted washcloth. Often children dislike the feeling of a wet washcloth that may be cold and irritate the sensitive ear. Typical washcloths are designed for scrubbing the whole body, meaning that they are thick and do not fit well in folds of the outer ear and the ear canal. Also, the scrubbing or wiping action of a washcloth may not remove all the dry skin, wax, and other debris as efficiently, gently, or completely gently as a purpose-built device.

Disposable wipes, while thinner than washcloths, are still not adapted to entering the small space of the ear canal and use a water, alcohol, or another liquid component as part of their cleaning action to remove ear wax and other debris. This liquid component may also cause children to experience discomfort due to the wet or cold feeling. Liquid could also get trapped in the ears leaving a residue or causing an earache through injury or infection. Disposable wipes are also not textured in a manner that can trap and remove dirt, debris, or wax.

Cotton swabs are often used for cleaning ears because they are well adapted to entering the ear canal. However, this ease of access can also cause injury to a degree that cotton swabs are not recommended to clean ears. The long and rigid nature of a cotton swab allows it to overextend into the ear canal and puncture the delicate eardrum. This causes immediate pain and can lead to hearing loss or infection. Children are more susceptible to ruptured eardrums either from their own inexperience or through the unfortunate accident of a parent who cannot know or feel how deeply they are extending the swab into their child's ear. Similar implements like bobby pins, straws, tweezers, pens, and pencils also have the same or greater drawbacks as cotton swabs.

Additional cleaning methods like candling or rinsing with a syringe of water require expert care to avoid injury.

The invention claimed here solves the problems of previous ones by allowing the user to safely clean their or their child's ear with a finger sleeve that traps dirt, debris, and wax without a minimal risk of user inflected injury. It is easily transportable and only requires one finger for use whereas many other inventions, such a cotton swab, require two or more fingers.

The claimed invention provides a finger sleeve for cleaning an ear including an elongated body with a closed end and an open end. The body is adapted to receive a finger extending through the open end towards the closed end. The closed end also has a flexible, non-rigid tip integral to the body that aids the removal of wax or other debris from the ear canal.

The body invention may be made of many materials, and preferably is made of an absorbent soft fabric material that may be either woven or nonwoven and bleached or non-bleached, sterile or non-sterile, and disposable or non-disposable. It can be made of but is not limited to cotton, polyester, rayon, cellulose, polyurethane, polyethylene, polyvinyl chloride, and other various co-polymers. It can be made of one ply or multiple plies and can be used on multiple sides if needed or desired by rotating it on the finger. It can be used damp, wet with water, or dry.

The texture of the cloth or other material of the body can vary. In the preferred embodiments, the body has a waffle weave or honeycomb texture. These textures are superior when it comes to cleaning and exfoliating because they remove more wax and debris than other fabrics. They are also softer, non-abrasive, more absorbent, faster drying, and more durable. Their texture also allows them to be thinner than other fabrics, which is preferred as it allows for a better fit in the ear.

Other textures, such as twill, flocked, jersey, or gabardine may be used alone or in combination with each other. Alternative textures may be useful for certain ears or may be more cosmetically appealing while still providing a superior clean than previous inventions. Combinations of textures may also be used to allow the user to benefit from the cleaning properties of multiple surfaces and remove dirt, debris, or wax that a single texture cannot remove.

In the preferred embodiment, the tip is formed from excess material from the body of the invention adjacent to the closed end. When the invention is woven and a seam exists extending from the open end to the closed end, excess material can be left adjacent to the tip while the rest of the seam material is removed from the hollow finger cavity. This allows for easier assembly of the invention. When the invention formed from a polyurethane or another material this tip can be formed in a mold. If the invention is hollowed out from a solid block, the tip could be formed from the excess of material between the hollow finger cavity and the closed end.

In one embodiment, the tip is affixed to the interior of the body adjacent to the closed end. This allows the tip to be made from a different material than the body. This can be a cotton ball, pompom, or a tip made from any natural or synthetic non-rigid material such as polyurethane.

In one embodiment, the textured material contains deep grooves on the closed end for trapping wax or other debris. The invention can also have ridges extending from the closed distal end. The ridges acting to dislodge wax or other debris that can then be trapped in the gap between these ridges or in adjacent grooves.

The grooves and ridges can be arranged in a decorative pattern or other design that may be pleasing to the user or their child.

While the invention has been described with respect to a human ear, it can be used for cleaning all mammalian ears, including, but not limited to, dogs, cats, and other pets who may not be able to remove dirt, debris, or wax without the assistance of their owner or other caregiver and this invention.

DETAILED DESCRIPTION OF THE DRAWINGS

Figure 1:
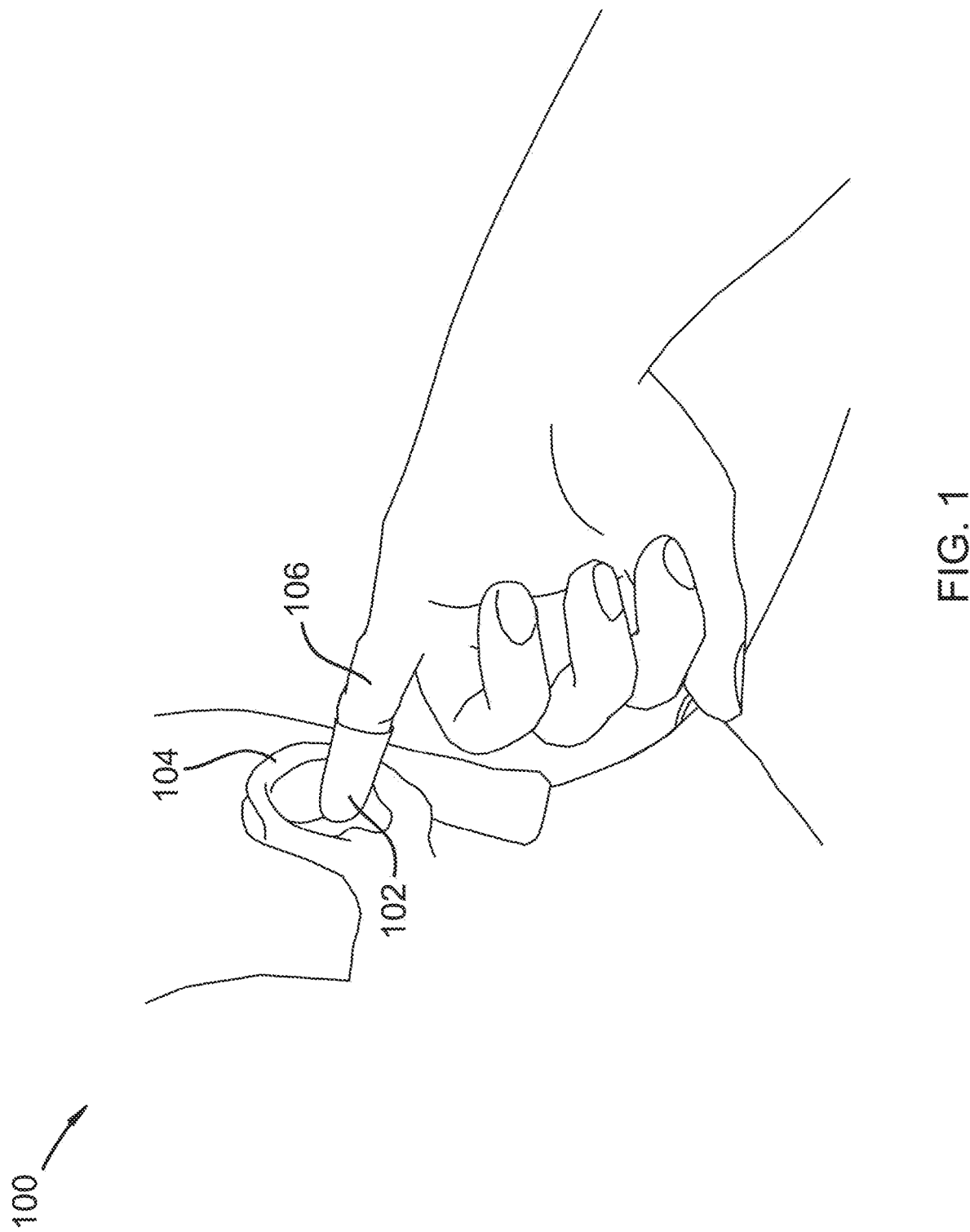
FIG. 1 is a perspective view of the finger sleeve when used to clean a user's ear.

FIG. 1 is a perspective drawing showing a user 100 cleaning their ear 104 with the invention 102 placed on the user's finger 106.

Figure 2:
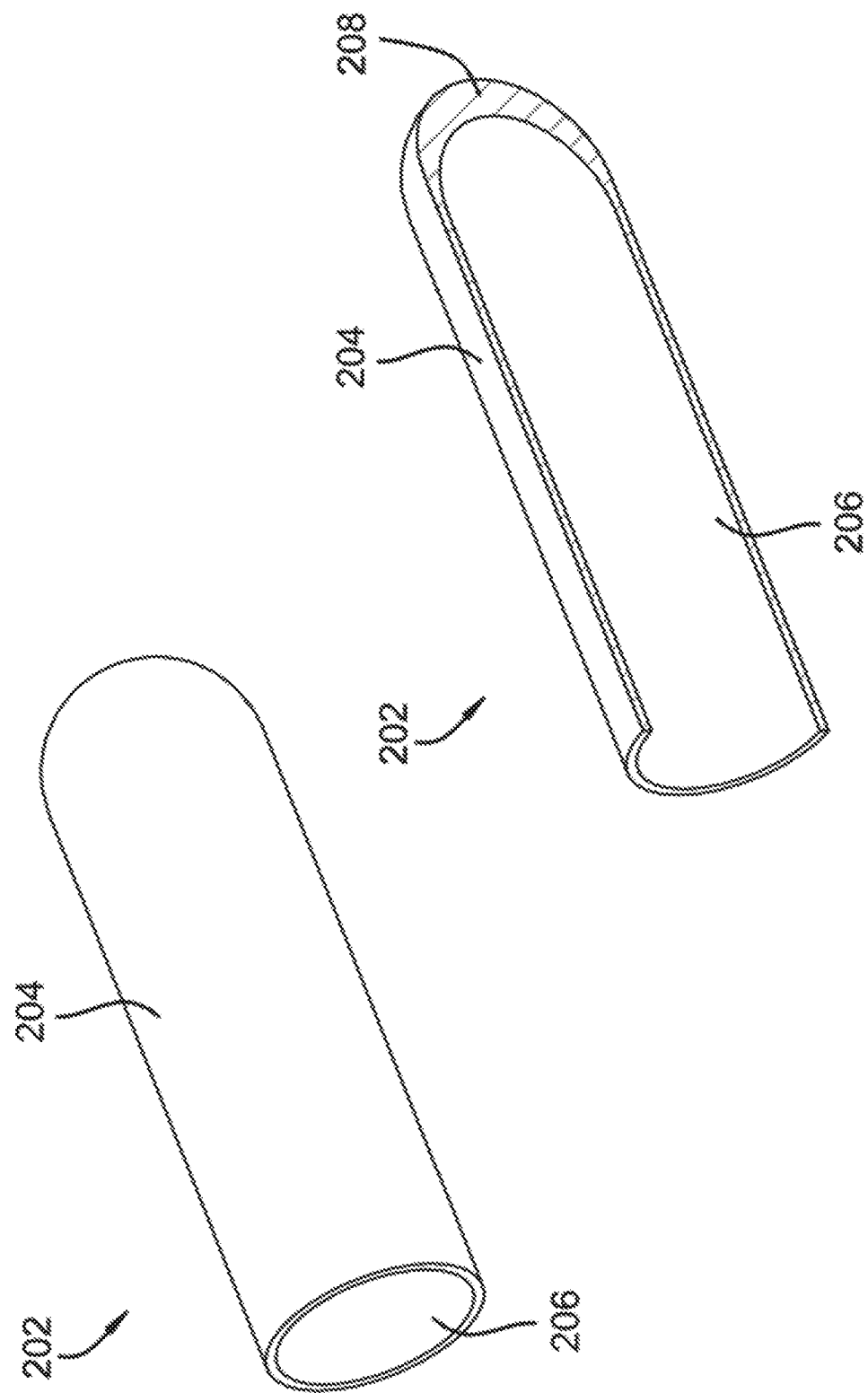
FIG. 2 is a plain view of the finger sleeve and a cross-sectional view.

FIG. 2 shows a plain view and a cross-sectional view of the finger sleeve 202. The tubular body of the finger sleeve has an interior 206 and an exterior 204 made of an absorbent, flexible material. The exterior 204 has can be adorned with images and patterns and has a textured finish that traps wax or other debris. The textured finish can be integral to the material of the body, for instance, if the body is made of woven fabric the texture would come from the weave of the material. The textured finish can also be imprinted into the exterior of the body through a mold or other process that produces a texture on the body's exterior. The body 202 extends in a longitudinal direction from a proximal open end to a closed distal end. The hollow cavity it creates is adapted to receive a human finger. Adjacent to the closed distal end is a tip 208 that is integral to or affixed to the closed distal end. The tip is comprised of a flexible material that can be the same or different from the material of the body.

Figure 3:
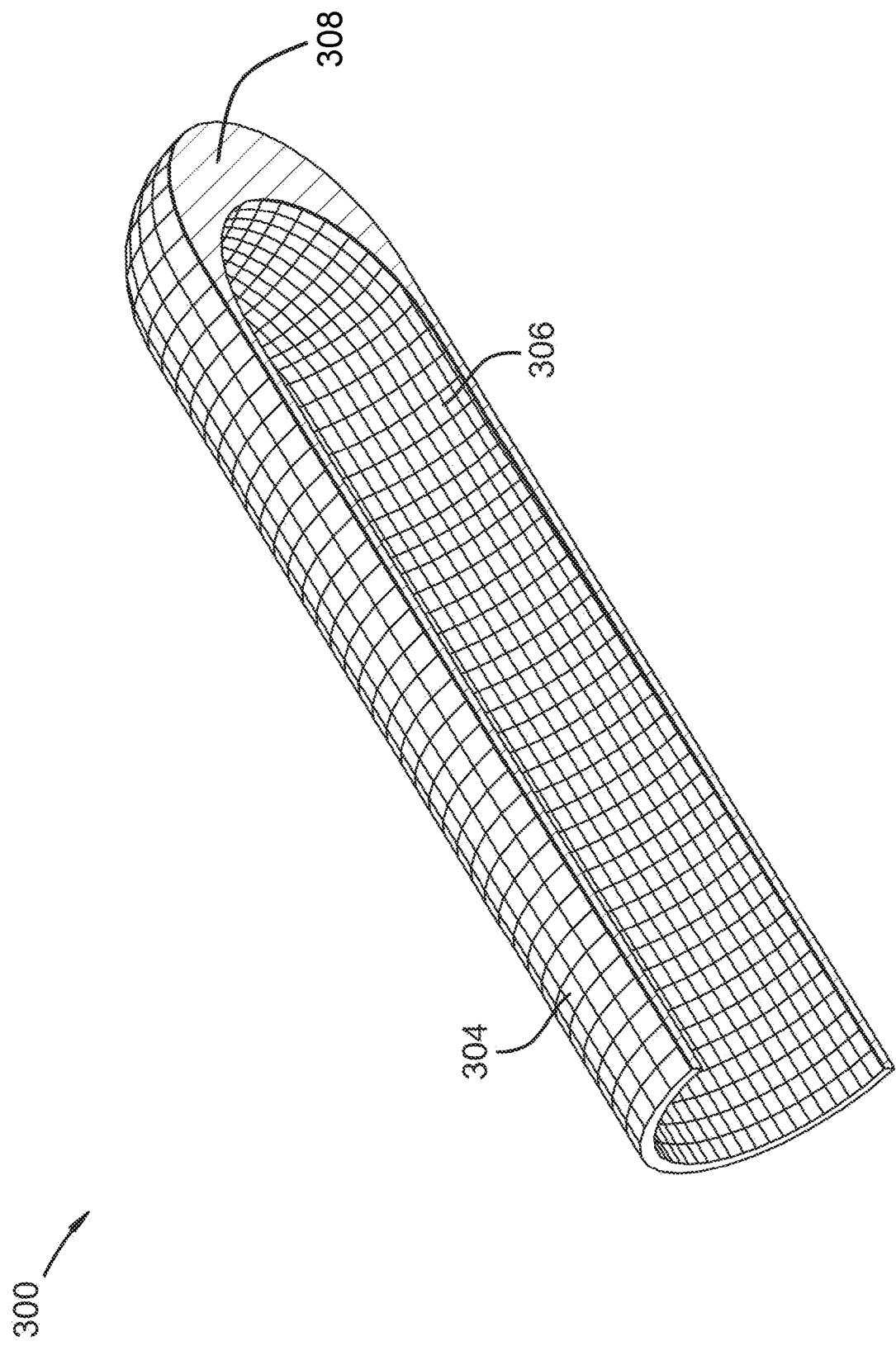
FIG. 3 is a cross-sectional view of the finger sleeve with an alternative textured construction.

FIG. 3 shows a cross-section view of an alternate embodiment of the finger sleeve 300. This embodiment has an alternative textured finish for the body that extends from the exterior 304 to the interior of the device 306. The flexible tip 308 at the closed distal end of the device is made up of the same material as the body.

Figure 4:
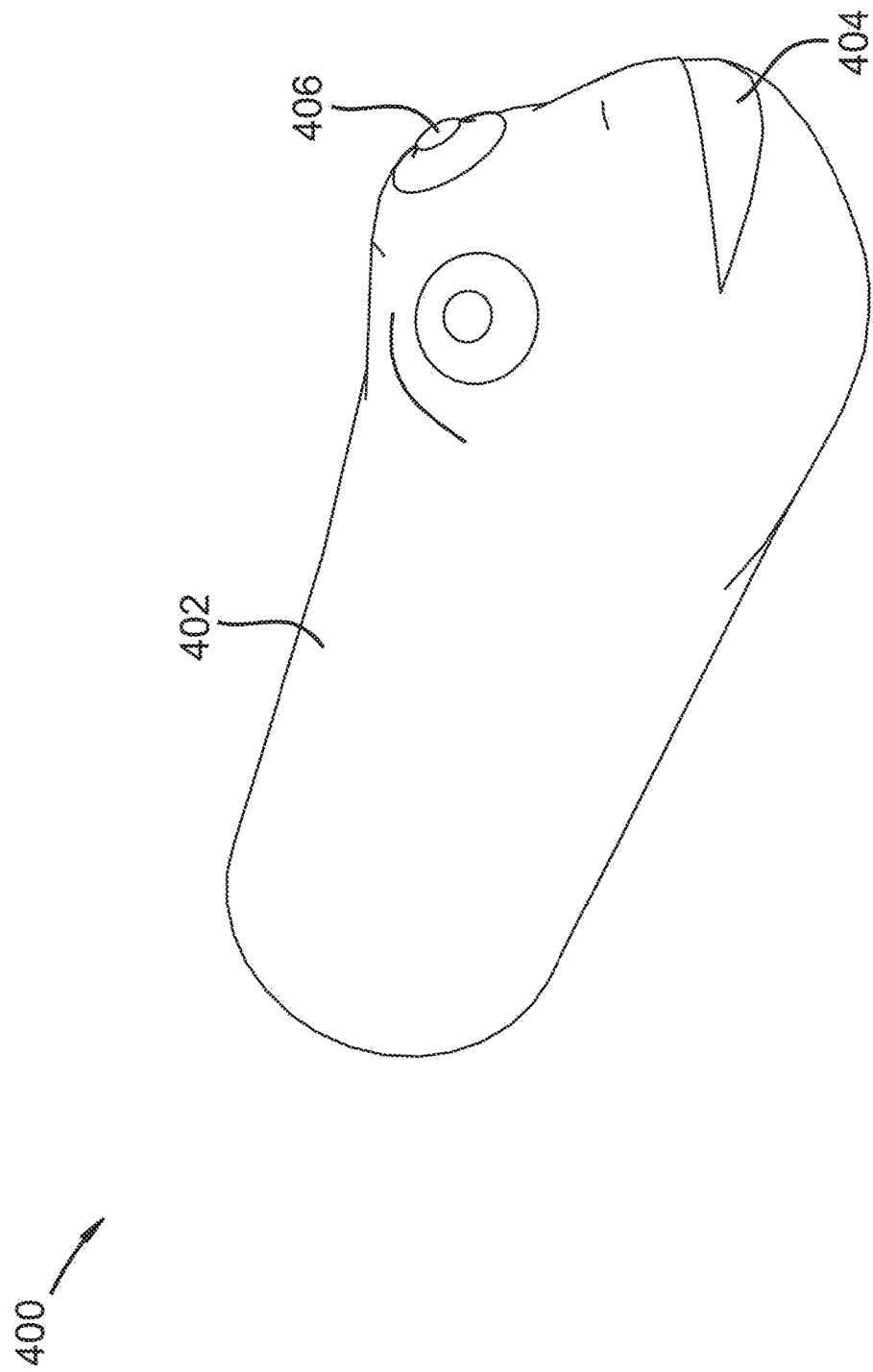
FIG. 4 is a view of one embodiment of the finger sleeve with grooves in the operative end in a decorative construction.
Figure 5:
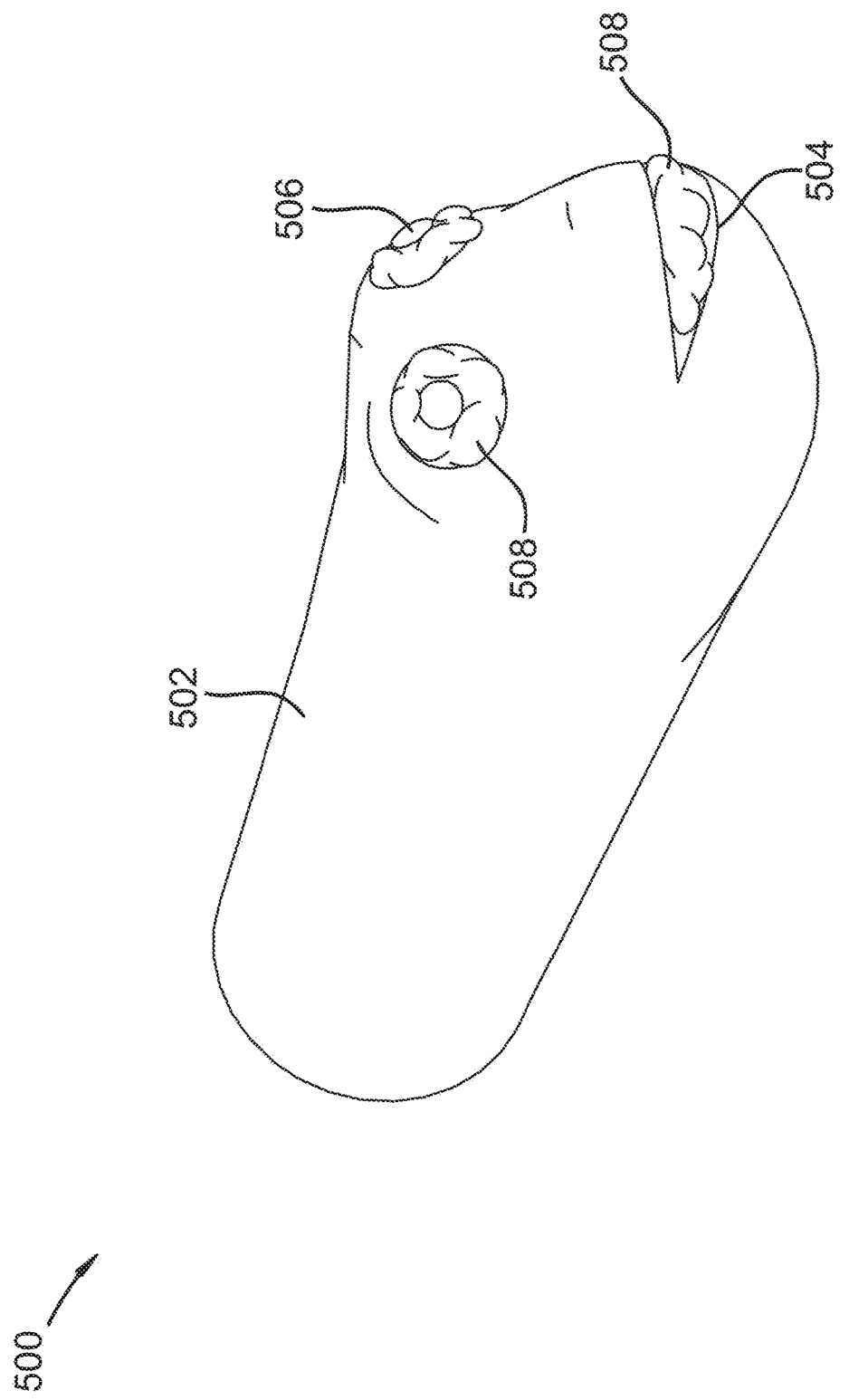
FIG. 5 is a view of the same embodiment of the finger sleeve demonstrating how wax or other debris is trapped in the grooves.

FIGS. 4 and 5 show a before and after image of an alternative embodiment of the finger sleeve. The body 400 and 500 contains grooves 404 and 504 and ridges 406 and 506 that dislodge wax and other debris and collect it 508. In this embodiment, the flexible tip is integrated into the body of the device and the grooves 404 and 504 are cut into it, molded from it, or made by some other means. The grooves can be made in such a way that it forms a decorative face or other design, in this embodiment it is a frog's face, that is pleasing to the user and children.

Figure 6:
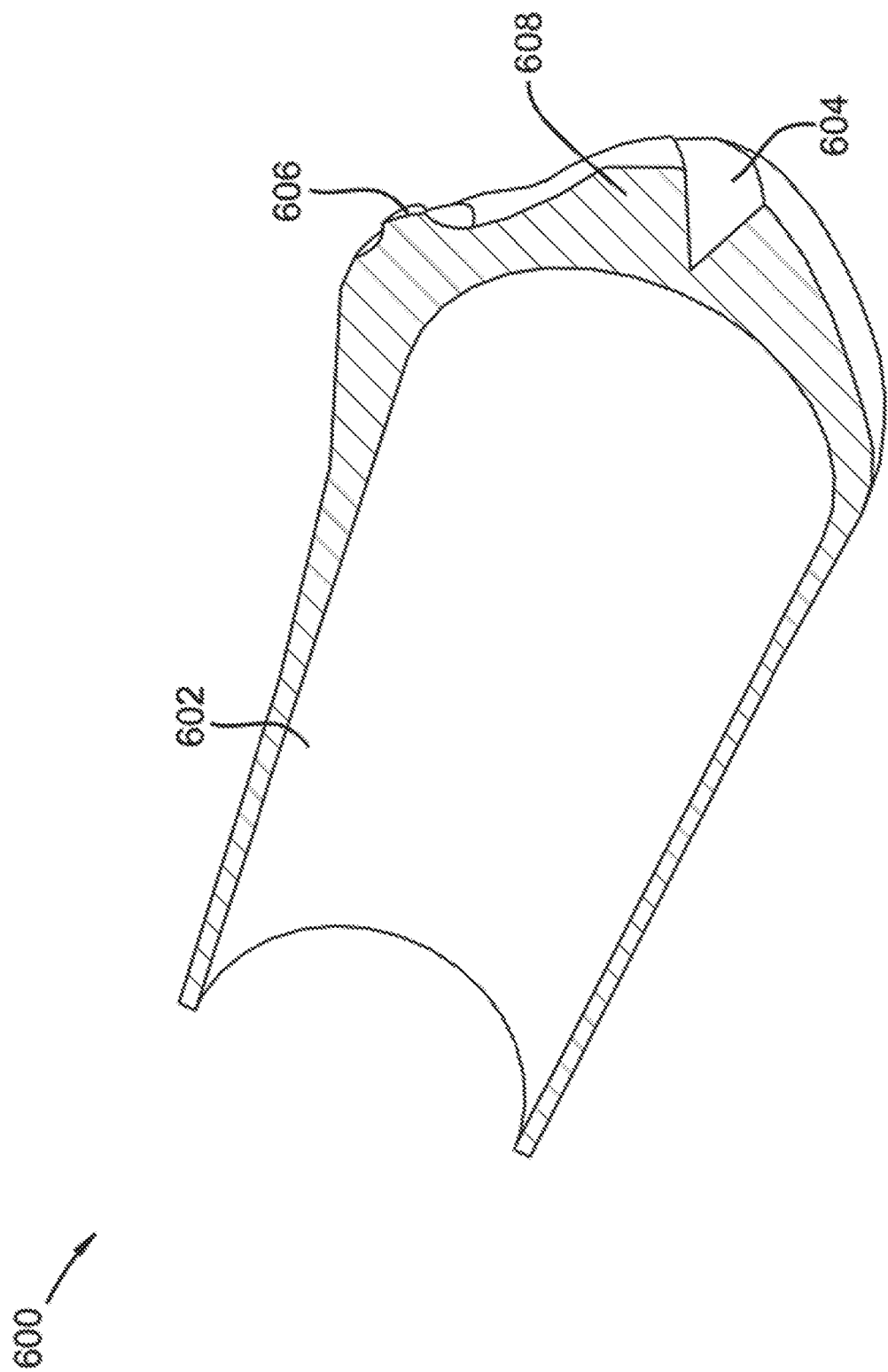
FIG. 6 is a cross-sectional view of the same embodiment of the finger sleeve with grooves.

FIG. 6 shows a cross-section view of an alternate embodiment of the finger sleeve 600. This cross-section shows the integrated tip 608 at the closed distal end of the device where the grooves 604 and ridges 606 are formed. The flexible tip is made up of the same material as the body.

While the invention has been described with respect to various presently preferred constructions, still other constructions may be suggested to those skilled in the art. The foregoing description should be construed to include all those embodiments within the spirit and scope of the following claims.

What is claimed is:

1. An ear-cleaner adapted for use on a user's finger, the ear-cleaner comprising:
    a waffle weave absorbent fabric tubular body with an internal seam and having
        an open proximal end, the open proximal end having a diameter adapted for receiving the user's finger;
        a closed distal end, wherein the internal seam extends from the open proximal end to the closed distal end;
        a hollow interior, the hollow interior adapted for receiving the user's finger extending through the open proximal end towards the closed distal end;
        an exterior, the exterior having a honeycomb texture formed from the waffle weave of the fabric; and
        a non-rigid tip adjacent to and forming the closed distal end, wherein the tip is formed by the waffle weave absorbent fabric tubular body and forming the extreme distal end of the ear-cleaner, wherein a greater amount of seam material of the internal seam is present at the closed distal interior than along the tubular body toward the open proximal end whereby the tip is formed of excess material at the closed distal end as a result of the internal seam.

2. An ear-cleaner adapted for use on a user's finger, the ear-cleaner comprising:
    a tubular body comprised of a woven absorbent textured fabric with an internal seam;
    the tubular body having an open proximal end, the open proximal end having a diameter adapted for receiving at least one of the user's fingers;
    a closed distal end, wherein the internal seam extends to the closed distal end;
    a hollow interior, the hollow interior adapted for receiving at least one of the user's fingers extending through the open proximal end towards the closed distal end;
    an exterior, the exterior having external ridges formed from the woven absorbent textured fabric; and
    a non-rigid tip integrated into and forming the closed distal end, wherein the tip is formed by the woven absorbent textured fabric tubular body and forming the extreme distal end of the ear-cleaner, wherein a greater amount of seam material of the internal seam is present at the closed distal interior than along the tubular body toward the open proximal end whereby the tip is formed of excess material at the closed distal end as a result of the internal seam.

3. An ear-cleaner as claimed in claim 2 wherein the ridges on the exterior of the tubular body are arranged in a decorative pattern.

4. An ear-cleaner adapted for use on a user's finger, the ear-cleaner comprising:

a waffle weave absorbent non-disposable woven cotton fabric tubular body with an internal seam and having:

an open proximal end, the open proximal end having a diameter adapted for receiving the user's finger;

a closed distal end, wherein the internal seam extends from the open proximal end to the closed distal end;

a hollow interior, the hollow interior adapted for receiving the user's finger extending through the open proximal end towards the closed distal end;

an exterior, the exterior having a honeycomb texture formed from the waffle weave of the fabric; and a non-rigid tip adjacent to and forming the closed distal end, wherein the tip is formed by the waffle weave absorbent non-disposable woven cotton fabric tubular body and forming the extreme distal end of the ear-cleaner, wherein a greater amount of seam material of the internal seam is present at the closed distal interior than along the tubular body toward the open proximal end whereby the tip is formed of excess material at the closed distal end as a result of the internal seam.

\* \* \* \* \*